United States Patent [19]

Manahan, Sr.

[11] Patent Number: 4,895,027

[45] Date of Patent: Jan. 23, 1990

[54] DETERMINING PLANE STRAIN FRACTURE TOUGHNESS AND THE J-INTEGRAL FOR SOLID MATERIALS USING STRESS FIELD MODIFIED MINIATURE SPECIMENS

[75] Inventor: Michael P. Manahan, Sr., Dublin, Ohio

[73] Assignee: Battelle Development Corporation, Columbus, Ohio

[21] Appl. No.: 145,830

[22] Filed: Jan. 19, 1988

[51] Int. Cl.$^4$ .............................................. G01N 3/08
[52] U.S. Cl. ........................................ 73/799; 73/794
[58] Field of Search ................. 73/799, 849, 794, 795, 73/799, 789, 798; 364/508

[56] References Cited

U.S. PATENT DOCUMENTS 4,567,774  2/1986  Manahan et al. ................. 73/849 X

OTHER PUBLICATIONS

Evgen'er, A. N. et al., DN-3M Equipment... Stresses, Weld. Prod. (G.B.), vol. 22, No. 7, Jul. 1975, pp. 50, 51.

Primary Examiner—Jerry W. Myracle
Attorney, Agent, or Firm—Watkins, Dunbar & Pollick

[57] ABSTRACT

A method of determining the mechanical behavior of solid materials by using stress field modified miniature specimens. The method is an improvement in the method of determining mechanical behavior information from specimens only so large as to have at least a volume or smallest dimension sufficient to satisfy continuum behavior in all directions. Mechanical behavior of the material is determined from the measurements taken during the loading of the specimen resulting in the formation of cracks and/or the further propagation of cracks in the miniature specimen. The specimens include construction features for applying additional stress field modifying loads upon the specimens during the test. These additional loads result in a desired stress state in the specimen which could not be achieved otherwise. A particular example is the introduction of a transverse tensile load during a bend test to increase the transverse stress field to achieve plane strain conditions in a thin specimen. The methods are useful in determining plane strain fracture toughness, dynamic plane-strain crack initiation and arrest fracture toughness, the J-Integral for the material, and the fracture mode transition behavior when the specimen thickness and volume is smaller than previously thought necessary.

23 Claims, 7 Drawing Sheets

CRACK OPENING DISPLACEMENT

FIG. 19

FIG. 20

DETERMINING PLANE STRAIN FRACTURE TOUGHNESS AND THE J-INTEGRAL FOR SOLID MATERIALS USING STRESS FIELD MODIFIED MINIATURE SPECIMENS

FIELD OF INVENTION

This invention relates to methods and apparatus for determining the mechanical behavior of solid materials and is especially useful for determining and measuring the mechanical behavior of materials when loaded or stressed for the purpose of establishing the design, use, safelife, and post-service criteria of the material. Although the term miniature is relative, as are all size descriptive terms, it is a fair characterization to define the field of this invention as the determination of the mechanical behavior of materials from miniature specimens, i.e., specimens noticeably smaller than prior conventional specimens in the materials testing field. More particularly, this invention relates to the testing of material specimens of thickness and volume less than thought necessary for valid determinations of plane strain fracture toughness ($K_{IC}$), more specifically, less than 2.5 $(K_{IC}/\sigma ys)^2$, specified by ASTM E-399-83. (1) This invention also relates to the testing of solid materials using specimens of thickness and volume less than thought necessary for valid determinations of the J-Integral and $J_{IC}$ specifically less than 25.0 ($J_{IC}/\sigma ys$), as specified by ASTM E-813-82. (2). This invention also relates to the testing of solid materials using specimens of thickness and volume less than thought necessary for valid determination of dynamic plane strain crack initiation ($K_{Id}$) and arrest ($K_{Ia}$) fracture toughness specifically less than $(K_{Ia}/\sigma yd)^2$ as specified in the draft ASTM standard entitled "Proposed ASTM Standard Test Method for Determining Plane-Strain Crack Arrest Fracture Toughness, $K_{Ia}$, of Ferritic Steels". This invention also relates to the testing of solid materials using specimens of thickness and volume less than thought necessary for valid determinations of fracture mode transition behavior (FMTB), specifically less than that specified by ASTM E23.

BACKGROUND OF THE INVENTION

Determination of the mechanical behavior physical properties of materials is necessary so that materials may be selected for use, evaluated when in use, and evaluated after use. From these determinations, decisions are made as to which materials to use, the conditions under which they can be used, and whether such materials in use can be continued to be used with safety. These types of determinations are particularly useful for determining the effects of environmental loading such as nuclear radiation on the mechanical properties of in-service materials. This invention is fully applicable to the determination of mechanical behavior of such materials but is also applicable to materials not subjected to radiation and the validity of the invention was demonstrated for materials not subjected to radiation.

The prior art includes U.S. Pat. No. 4,567,774 having the inventor, Michael P. Manahan, common with this application, and assigned to the same assignee. This earlier patent, hereinafter referred to as the "prior patent" includes the basic concepts upon which this invention is based. The disclosure of the prior patent is included herein by reference and the portions of that disclosure not specifically needed for the disclosure of this improvement invention are not included herein. However, reference to the prior patent may be helpful to the understanding hereof.

In the past, the most common procedure has been to determine the mechanical behavior of material by testing large samples that are either created more or less simultaneously or side by side with the product that is intended to be used or are cut from the same batch of material. In the determination of the mechanical behavior of solid materials and particularly metals, the practice is to make tensile, fatigue, creep, stress relaxation, fracture mode transition behavior, fracture toughness, etc. specimens; and these are then subjected to loads while measurements are taken of the force, time, displacement, energy, velocity, temperature, crack length, etc. of the specimen. Information on stress and strain, which can be thought of as normalized load and deflection, respectively, as well as other useful parameters are then obtained by simple mathematical operations. For example, in a uniaxial tensile test, the stress is determined by dividing the measured load by the specimen cross sectional area.

While this may be satisfactory in most instances, there are other circumstances such as the post-irradiation testing of materials used in nuclear reactors where samples may be unavailable in sufficient size and quantity to carry out these destructive tests during the life of the materials in use. In general, neutron irradiation space for materials investigations is limited and costly. It is, therefore, desirable to use specimens of minimum volume. Since neutron irradiation costs scale with specimen volume, miniaturized mechanical behavior testing can provide significant savings in irradiation testing costs for nuclear materials investigations. In addition, it is possible to provide mechanical behavior information which is not ordinarily obtainable due to space limitations in irradiation experiments and thus expedite alloy development investigations. Of course, miniature specimen testing is applicable to materials investigations for other nuclear technologies as well as non-nuclear technologies requiring mechanical behavior characterizations from a small volume of material. One such non-nuclear application is cutting small pieces of material from in-service components and using miniature specimens to measure the current mechanical behavior state. These data can then be used to estimate the remaining life of the in-service component.

There are four principal conceptual innovative aspects to the miniaturized fracture testing method of this invention. The first is the use of specimens that are significantly thinner and smaller than those currently in use. The second is the use of the appropriate loading configuration to either accommodate the size scale involved or better represent the actual in-service loading. The third is to modify the stress field in the specimen (caused by loading the specimen in a manner analogous to the current practice) by applying additional stressing force to the specimen so as to induce stress in the specimen in a selected orientation. This is done so as to achieve or closely approximate a desired stress state in the specimen which could not be achieved in any other way. A particular manifestation is to induce a large transverse stress normal to the conventional test loading direction which approaches a plane strain condition in a thin specimen. The rate and magnitude of the additionally induced stress is related to the rate and magnitude of the conventionally applied load on the specimen. The stress field modification in effect is used to replace the need for material thickness. The fourth is the use of the finite element method to calculate the direction and amount of additional load to be applied to achieve the desired stress state in the specimen. In a particular manifestation, the finite element code is used to determine the amount of transverse load to be applied to achieve plane strain conditions as a function of the vertically applied load for a three point bend or compact type specimen.

This invention improves upon the method of U.S. Pat. No. 4,567,774 by teaching the modifying of the stress field during fracture behavior testing with the miniature specimen. This modifying of the stress field can be done mechanically or by using a force field such as a magnetic field in order to produce stresses in preferred orientations in the material. In essence, the stress field modification replaces the need for material thickness and can minimize the need for side grooving to attain valid fracture toughness data.

Current test procedures require a minimum specimen thickness for plane strain fracture toughness testing which cannot be satisfied in many cases. This has historically served to preclude use of miniature specimens. The advantage of the present invention is that specimens which are much thinner than those currently in use can be accurately tested. This enables testing of materials removed from in-service components in cases where it is not possible to remove enough material to meet current ASTM test requirements. Another advantage of the method of the invention is that the method may allow the modifying of the stress field such that mixed mode fracture in the transition region can be avoided and/or conservatively accounted for. The invention can in many instances eliminate the need for side grooving now needed for accurate testing with many materials.

Another advantage of the present invention is that in-service stress fields can be simulated in the laboratory thereby providing data which is more representative of component performance.

SUMMARY OF THE INVENTION

The invention involves modifying the stress field near the crack tip during fracture testing with a miniature specimen. This modifying of the stress field can be done mechanically or by using a force field such as a magnetic field to produce stress in preferred orientations in the material. In essence, stress field modification replaces the need for material thickness and minimizes the need for side-grooving to attain valid fracture behavior data.

The following observations can be made regarding size effects present in conventional fracture testing:

1. The plastic zone size depends on the stress state near the crack tip.
2. For thick samples a large transverse stress is generated which resists plastic deformation in a direction parallel to the crack front.
3. Plastic zone size is smaller under plane strain conditions by approximately a factor of three.(3)

$$ry \approx \frac{1}{2\pi} \left( \frac{K}{\sigma ys} \right)^2 \text{ plane stress}$$

-continued $$ry \approx \frac{1}{6\pi} \left( \frac{K}{\sigma ys} \right)^2 \text{ plane strain}$$

4. Fracture toughness ($K_{IC}$) depends on the volume of material capable of plastically deforming prior to crack advance. This volume depends on specimen thickness (B).

5. Above a certain thickness, the fracture toughness ($K_c$) equals the plane strain fracture toughness ($K_{IC}$) and a constant $K_{IC}$, $K_{Id}$, $K_{Ia}$ is obtained.

$K_{IC}$, $K_{Id}$, $K_{Ia}$, depend only on metallurgical factors while $K_c$ depends on geometry as well as metallurgical conditions. Since $K_{IC}$, $K_{Id}$, $K_{Ia}$, depend only on metallurgical conditions and is the lower toughness, it is of the higher engineering significance.

This invention is directed to solving the specimen size effects problem in fracture toughness testing. The invention may enable restricting fracture to a prescribed mode. The invention therefore may solve the problem of mixed mode fracture in the transition region for certain materials.

The invention comprises a process of determining mechanical behavior of solid materials, including:

(a) providing a specimen of the material having a volume and smallest dimension sufficient to establish continuum behavior in all directions, and with a volume not more than $10^7$ times said sufficient volume;

(b) modifying the stress field of the specimen by applying stressing loads to the specimen so as to induce a desired additional stress field in the specimen;

(c) measuring plane strain or nearly plane strain fracture toughness ($K_{IC}$), dynamic plane strain crack initiation ($K_{Id}$) and arrest ($K_{Ia}$) fracture toughness, the J-Integral, and FMTB;

(d) determining the behavior of the material from the measurements taken according to the principles of the finite element method and/or the principles of linear or nonlinear material mechanics or both. The invention includes carrying out the process by using a code which is constructed according to the finite element method.

An object of this invention is to provide a method of determining the mechanical behavior of solid materials from specimens with only sufficient volume and smallest dimension to satisfy continuum behavior in all directions. While a variety of loading configurations are possible, it is a feature of this invention to provide a method of determining the fracture behavior of solid materials accurately by bending miniature specimens while applying a through thickness directed load designed to approach plane strain conditions. Still a further feature is to determine the fracture behavior accurately by the finite element method, particularly when a modified stress field has been applied along with the miniature bend test load.

Another feature is to determine the fracture behavior by the processes of continuum material mechanics carried out by a code which is applied according to a predetermined algorithm which has been determined to be accurate.

An overall object of the invention is to provide the capability of determining fracture behavior of material through a process requiring substantially less material and smaller specimen thicknesses than used with conventional techniques, and a process using specimen sizes so small that they may be trepanned from the elements of existing structures without significantly altering the overall characteristics of the structures.

The foregoing and other advantages of the invention will become apparent from the following disclosure in which preferred embodiments of the invention are described in detail and illustrated in the accompanying drawings. It is contemplated that variations in structural features and arrangement of parts may appear to the person skilled in the art, without departing from the scope or sacrificing any of the advantages of the invention.

DETAILED DESCRIPTION OF THE INVENTION AND BEST MODE FOR CARRYING OUT THE PREFERRED EMBODIMENT

Figure 1:
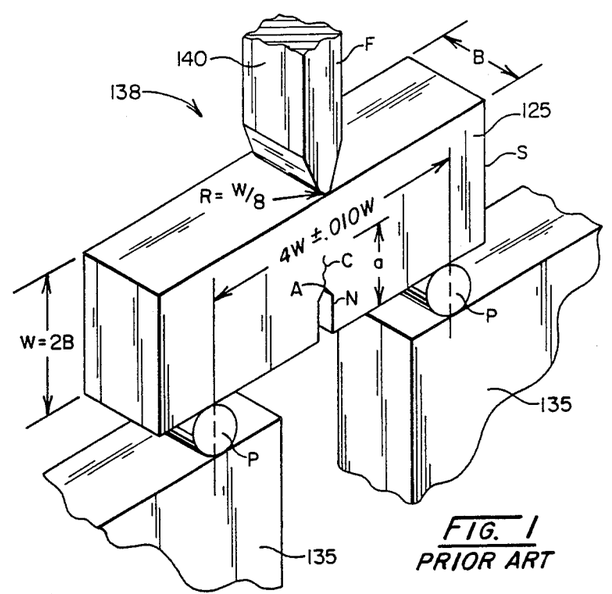
FIG. 1 is a perspective view of the fixture and one of the specimens employed in the standard ASTM bend test to determine fracture toughness.

Referring to FIG. 1, a prior art method for determining the plane strain fracture toughness ($K_{IC}$) and the J-Integral of a solid material is carried out on a specimen 125 in an apparatus, indicated generally as 138. The apparatus 138 includes a punch 140 having a radius tip R and a pair of roller pins P supported on a frame 135.

The specimen 125 is dimensionally prescribed by ASTM standards such as ASTM E813-81 or ASTM E399-83. The thickness (B) of a specimen depends on the material of the specimen that is being tested. For ordinary materials to which the test in ASTM E399-83 can be applied, both the specimen thickness B and crack length is required to exceed 2.5 $(K_{IC}/\sigma ys)^2$. In order for $J_{IC}$ and the J-R curve to be valid according to ASTM E813-81, the ASTM requires that the initial ligament b ($b=W-a$) and specimen thickness B must be greater than 25 $J_{IC}/\sigma ys$. The draft ASTM crack arrest standard prescribes that B must equal or exceed $(K_{Ia}/\sigma yd)^2$, where $\sigma yd$ is the dynamic yield strength. This invention enables testing at specimen widths below these ASTM requirements and yet provides fracture behavior data comparable to that obtained by following ASTM requirements.

With the establishment of the specimen thickness, other key specimen dimensions are multiples of B and are prescribed by ASTM. Other specimen geometries for fracture testing are described by the ASTM and the invention can be used with these generic geometry types (with appropriate modifications) in a manner analogous to that described herein for the three point bend geometry.

The publications of the American Society of Testing Materials (ASTM) Designation: E399-83 and E813-81 are included herein by reference with special attention to FIGS. A3.1, A3.2, A4.1, A5.1, A5.3 of E399-83 and to FIGS. 2, 5, and 6 of E813-81. The draft ASTM crack arrest standard is also included herein by reference with special attention to FIGS. 1, 5 and 7. A Notch N is provided in the specimen of FIG. 1 on the lower face near the center and a crack is induced by well known fatigue pre-cracking procedures to induce a crack C to begin near the apex A of the notch N. In the prescribed method of the ASTM standard a vertical downward force is applied on the top of the specimen 125 at a point of approximately equal distance between the central longitudinal axes of the pins P. A plurality of samples are tested at different temperatures to determine the value of Kc at which the crack just begins to propagate in the material and to determine the resistance of the material to further crack propagation.

It has been previously thought that this prescribed method would not provide valid plane strain fracture toughness data if the specimen is smaller than that prescribed by the ASTM standards. However, by the methods and apparatus of this invention it has been demonstrated that valid plane strain fracture toughness data can be found and used.

As explained in the prior patent the use of miniature specimens greatly increases the ability to determine the usefulness of materials in-service as such specimens can be taken from some structures insitu without deterring the integrity or performance of the structure.

Figure 2:
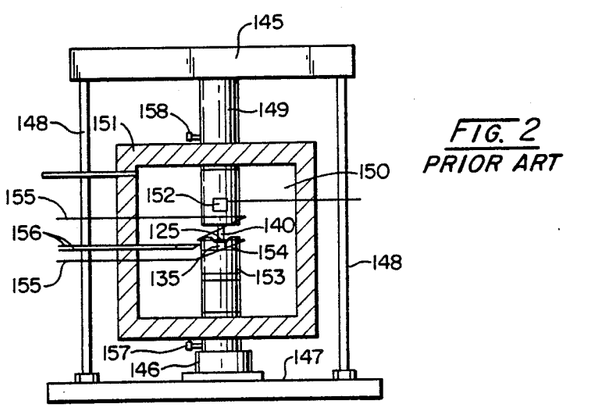
FIG. 2 is a schematic elevational view of the apparatus in which the standard test and the method of this invention is employed.
Figure 3:
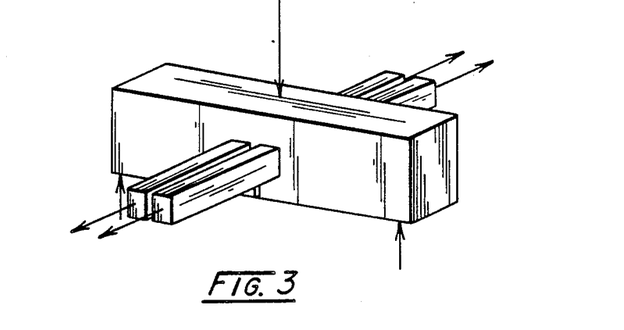
FIG. 3 is a schematic perspective view of the preferred embodiment of the specimen of this invention.
Figure 4:
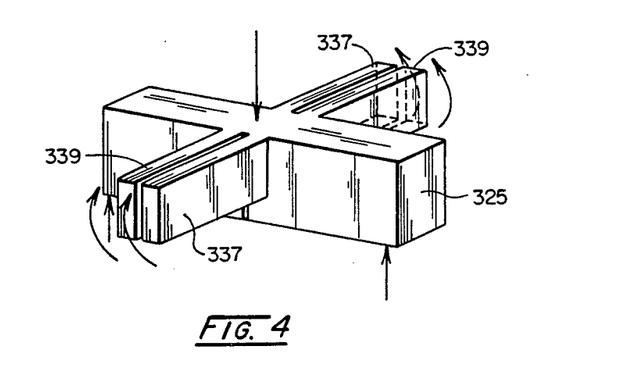
FIG. 4 is a schematic perspective view of another embodiment of the specimen employed in this invention.

Referring to FIG. 2 the method of this invention is carried out in apparatus similar to that shown in the prior patent. Included in the typical practice of the invention is the measurement of key variables such as the time variation of the load L, the time variation of the displacement D, the velocity of the punch 140, the temperature of the specimen 125 and its environment, crack initiation and propagation by means of the electricpotential (EP) technique or suitable means, and the crack opening displacement as determined by a calibrated clip gage or other suitable means. Apparatus to control and measure these factors is shown in FIG. 2, in which a conventional compression loading test apparatus of the "Instron" or "MTS" type includes a crosshead 145 oppositely disposed to an actuator 146 and connected thereto by tension members 148. The actuator 146 is operated upward from a frame/platform 147. Tension members 148 connect the crosshead 145 and the frame 147.

A water cooled upper compression rod 149 extends into an environmentally controlled chamber 150, surrounded by an insulated wall 151, and supports a water cooled load cell 152 that carries the punch 140. The specimen 125' of this invention is supported beneath the punch 140 on the pins P as shown in FIG. 1. The frame 135 is carried on a thermally insulated water cooled compression rod 153 which is supported on the actuator 146. An induction heating coil 154 or resistance heating device surrounds the area of the specimen 125, fed by inlet and outlet connections 155. At least two thermocouples 156 are attached to the specimen support 135 and one additional thermocouple measures the environment temperature near the crack tip.

Axial extensometers 157 and 158 are connected to the compression rods 153, 149 respectively, so that the measurements may be made of key variables such as the distance traveled by the specimen 125' and bending displacement in the specimen 125'. The temperature of the specimen 125 and the surrounding area can be controlled by the induction heating coil 154 and the thermocouple 156. As necessary the environment in the chamber 150 can be controlled by the admission of inert or other gas or liquid. A stroke transducer is provided in the Instron equipment to measure the velocity of the punch 140 relative to the sample 125.

In the practice of the process of this invention, a specimen is provided of a solid material having at least a volume and smallest dimension sufficient to satisfy continuum behavior in all directions. In many ductile metal materials this volume and smallest dimension will be determined by the largest microstructural heterogeneity and the fact that approximately 5 to 15 times the size of the microstructural feature usually represents a lower boundary necessary to achieve continuum behavior.

In general, the uncracked ligament b must be large enough so that the region of intense stress and strain caused by the presence of a crack is contained within the specimen. In cases where the J-Integral vs. crack extension ( a) is determined, referred to as the J-R curve, the uncracked ligament b should be large enough to obtain reasonably accurate crack extension data. In materials which fracture by a trigger particle mechanism (4), it may be desirable to size the uncracked ligament b so that a statistically significant volume of material is sampled. These additional considerations, while still yielding miniature specimens in most cases, need not be applied in the practice of the invention. However, these considerations may yield more accurate miniature specimen data for some materials.

The continuum behavior minimum size limit is the point where there is no variation in the average mechanical behavior response when a larger number of grains is used. The threshold limit of the successful practice of this invention, from a miniaturization standpoint, is that size below which continuum behavior in all directions is not certain to take place. To obtain the benefits of miniaturization it is not necessary to provide a specimen exactly at the minimum theoretical limit to satisfy continuum behavior. Specimens having dimensions smaller than this size limit, if desired, can be tested using the miniature specimen approach. Specimens having at least a volume and smallest dimension to satisfy continuum behavior in all directions and with the volume not more than $10^7$ times that sufficient volume can be successfully used in processes of the invention to accurately represent large conventional specimen behavior.

It is believed that this invention applies over specimen thicknesses from the continuum limit to the prior art specimen thickness requirement described earlier. The upper limit for the successful practice of the invention in a miniature bend test is not known to be a precise physical limit, and may depend more on obtaining the practical benefits from determining mechanical behavior by specimens of limited size.

In a typical preferred embodiment of the practice of the invention, results have been obtained which demonstrate the efficacy and accuracy of the method. Using the apparatus of FIGS. 2 and 11 and the specimens shown in FIGS. 5, 6, 7, 8, 9, and 10, and 11 unirradiated fracture behavior information was obtained from such miniaturized samples.

In the practice of the method of this invention with specimens according to this invention it has been found that reliable values of $K_{IC}$ and the J Integral can be found using miniature specimens. Within the term "miniature" as used herein, specimens have been tested using a thickness B which is less than that permitted for a given material under the ASTM standards. To accomplish this, it has been conceived and proven that the plane strain conditions required for valid testing and results can be closely approximated by modification to the edge and near edge conditions of the test specimen, on the sides, in positions juxtaposed to the crack C and the inside extremity of the notch N.

In the prior art ASTM test, the thickness B is established to be large enough that plane strain conditions exist or nearly exist across the thickness of the specimen near the apex A of the crack C. On the otherhand, when the thickness B comes too small, as in the testing of miniature specimens, constrained conditions no longer exist or are substantially reduced near the edges of the specimen in the vicinity of the crack.(3)

In the method of this invention, the transverse stress field (in the thickness direction) in the vicinity of the notch and crack is modified so that nearly plane strain conditions prevail over most of the specimen cross section. It is believed that the modified stress field may be induced by various means such as by side pull, side moments, or magnetically induced stress concentrations.

Figure 5:
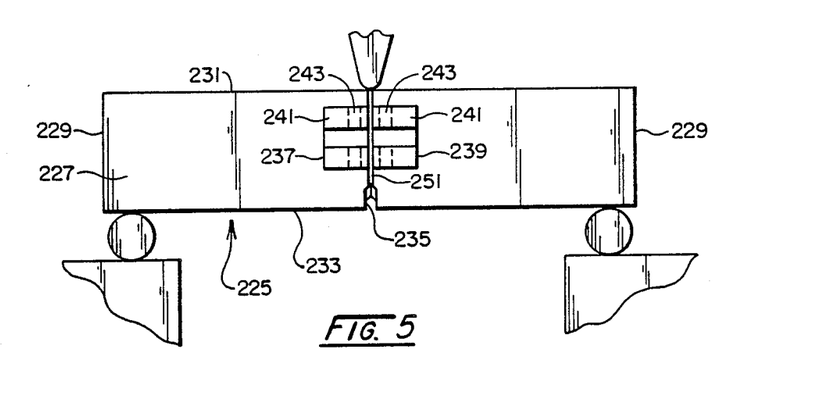
FIG. 5 is an elevational view of a specimen employed in the practice of the method of this invention.
Figure 6:
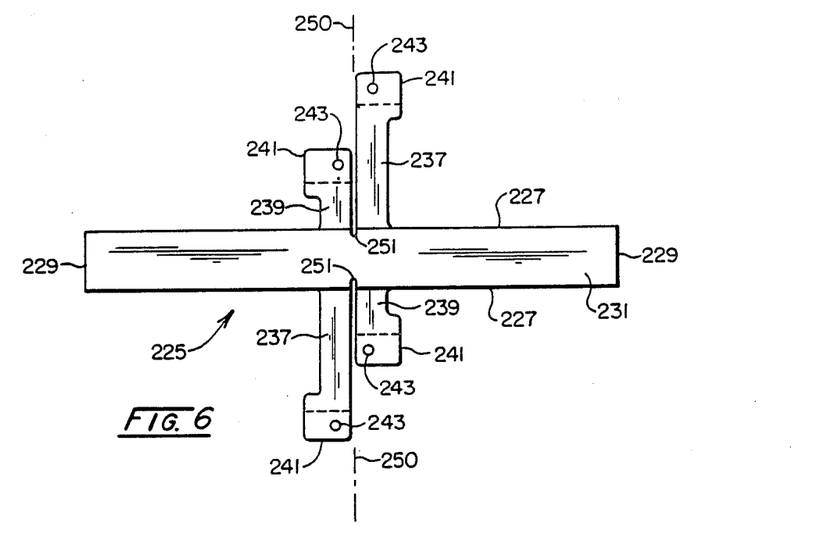
FIG. 6 is a plan view of the specimen employed in the practice of the method of this invention.
Figure 7:
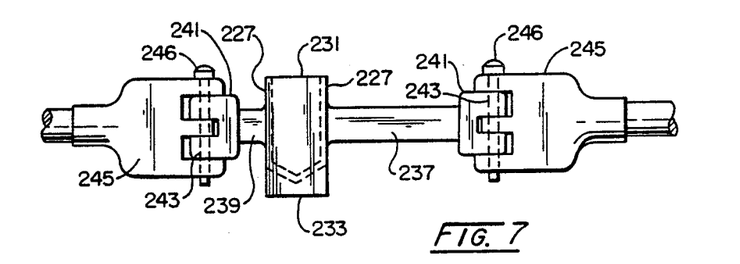
FIG. 7 is an elevational end view of the specimen shown in FIGS. 5 and 6.

Referring to FIGS. 5, 6, and 7, in a preferred embodiment of the invention, the side pull method and specimen is demonstrated. A beam specimen 225 is rectangular and has rectangular sides 227, rectangular ends 229, and a generally elongated top 231. At the bottom surface 233, a notch 235 is provided near the center between the ends 229 and the specimen can be pre-cracked. As most clearly seen in FIG. 6, each side 227 is provided with a pair of longer side arms 237 and shorter side arms 239. Each side arm is provided with an enlarged buttress portion 241 including an aperture 243 for attachment to a servo hydraulic test machine by pinning.

As shown in FIG. 7, the buttress portion 241 and apertures 243 are provided for the attachment of clevis connectors 245 and pins 246. The side arms 237 and 239 are juxtaposed and closely spaced from the longitudinal center line of the specimen 50, and are formed as an integral part of the specimen 225. The side arms 237, 239 are either machined from a solid block of material or are welded or otherwise attached.

Figure 8:
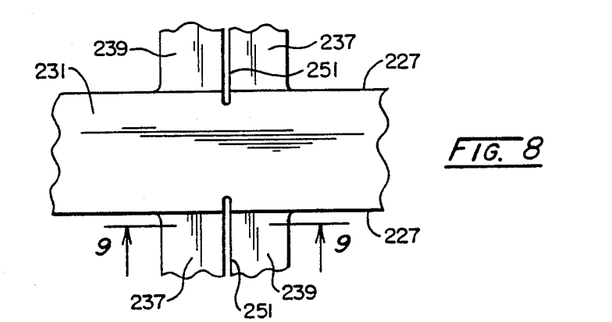
FIG. 8 is an enlarged view of a portion of the plan view shown in FIG. 6.

Referring to FIG. 8, side arms 237 and 239 are slightly separated by a groove 251 in each side 227. The grooves 251 may extend a short distance laterally into the sides 227 and longitudinally from the top 231 to the bottom 233. These grooves are provided to define the specimen thickness and to ensure that the starter crack propagates between the arms.

Figure 9:
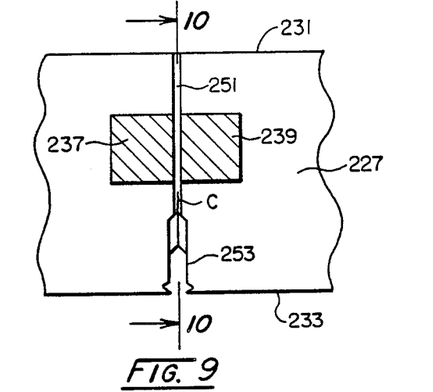
FIG. 9 is an enlarged view of a portion of the specimen shown in FIGS. 5, 6, and 7 showing a notch detail.
Figure 10:
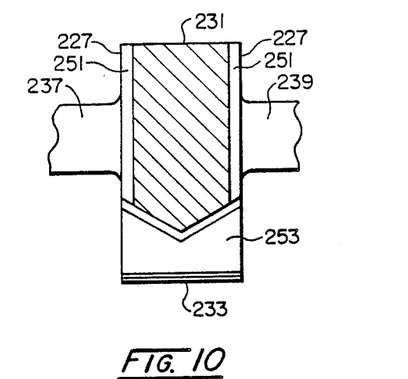
FIG. 10 is a section view taken along the line 10—10 of FIG. 9.

Referring to FIGS. 9 and 10 a preferred shape of the possible notch geometrics for the notch 235, which is well known to those skilled in the art and specified in the ASTM(1) standards is that of a "chevron" notch shape, including angularly divergent side portions 253. At the entrance to the notch 253, it is conventional practice to provide a pair of lip portions 254 for the attachment of spring loaded tines carrying strain gages to record the change in distance in the movement of the lips when the load is applied at the opposite top side of the specimen 225.

Figure 11:
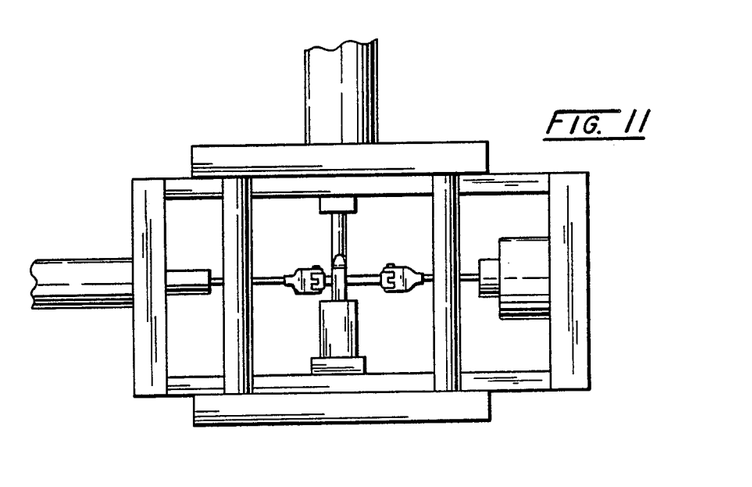
FIG. 11 is an enlarged elevational view of the specimen of FIGS. 5, 6, and 7 in the test fixture showing the vertical and transverse load fixturing.
Figure 12:
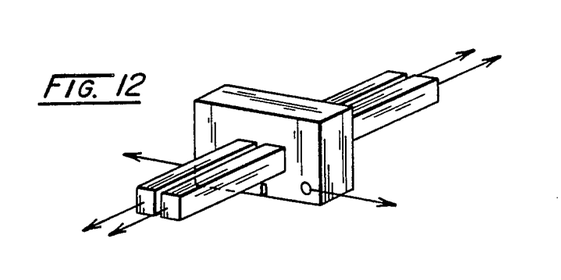
FIG. 12 is a perspective view of another embodiment of a specimen used in the method of this invention.
Figure 13:
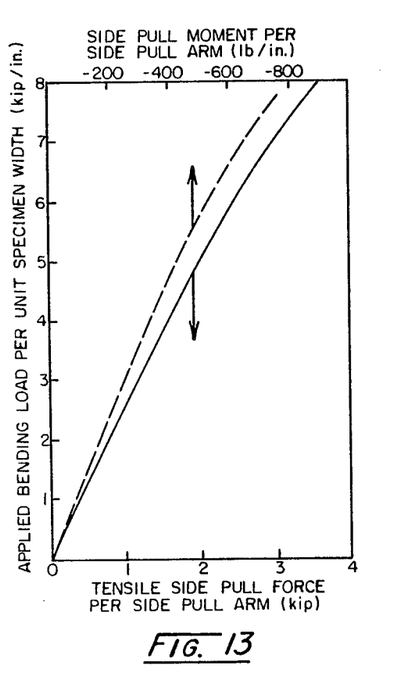
FIG. 13 is a graph showing the finite element results which prescribe the amount of side pull force (or alternatively, the amount of side moment) as a function of the vertical applied load necessary to modify the stress field to approximate plane strain conditions in the miniature specimen. This result applies to nuclear grade ASTM A508 steel tested at 175° F.

In the practice of the invention, the specimen 225 is placed in the apparatus shown in FIGS. 2 and 11 at the same position as the prior art specimen 125 in the prior practice. Clevises 245 are attached to the side arms 237 and 239. Equal and opposite tension first loads are applied laterally through the clevises, away from the longitudinal center plane of the specimen, simultaneously with the application of the second load through the punch 140. The tensile forces applied to the sides of the specimen 225 are juxtaposed to the plane of crack propagation and modify the stress field. The relationship between the vertical applied second load and the side pull first load is calculated by the finite element method as shown in FIG. 13. It has been found that this tension force so modifies this stress field that nearly plane strain conditions exist to the extent that acceptable tolerances between the fracture toughness value $K_{IC}$ and J Integral of small specimens and those provided in standard ASTM enlarged specimens are obtained.

The material chosen for the tests was a nuclear grade ASTM A508 steel (TSE6). The raw data obtained during the test include parameters of load, punch displacement, crack opening displacement, and temperature.

Figure 14:
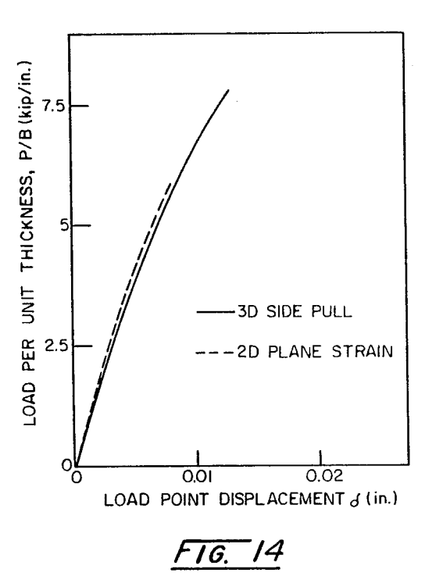
FIG. 14 shows a plot of the finite element model of calculated applied vertical load per unit thickness vs load point displacement for a nuclear grade ASTM A508 steel tested at 175° F.
Figure 15:
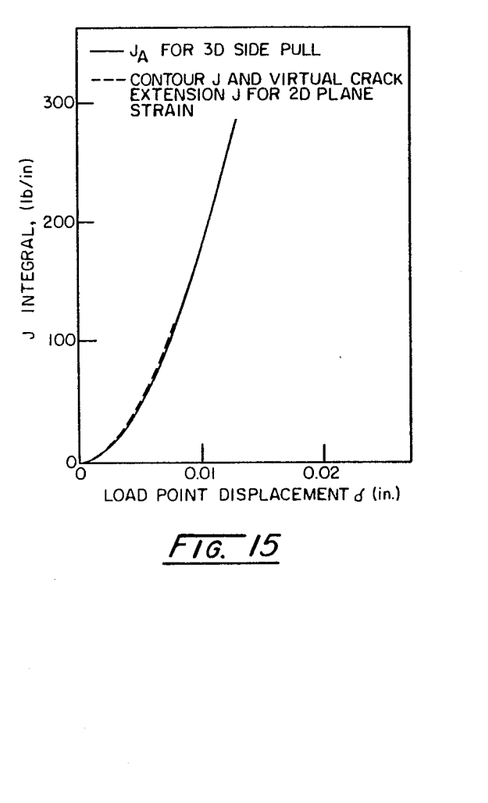
FIG. 15 shows a plot of the finite element model calculated J Integral vs. load point displacement for a nuclear grade ASTM A508 steel test at 175° F.
Figure 16:
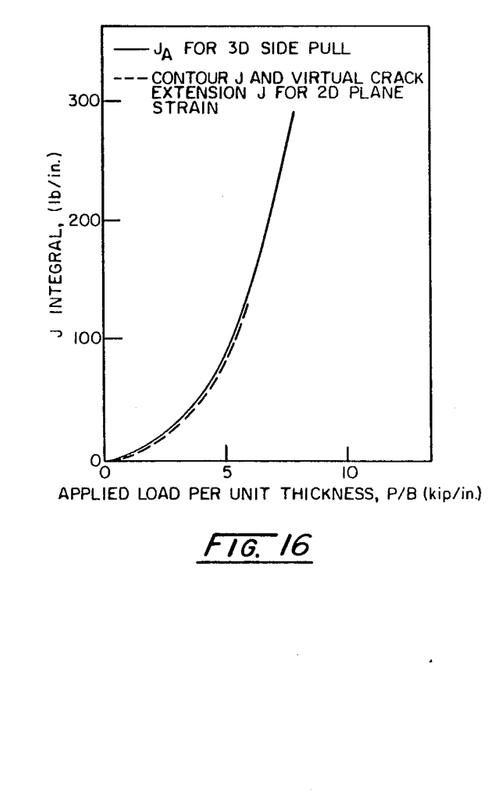
FIG. 16 shows a plot of the finite element model calculated J Integral vs applied load per unit thickness for a nuclear grade ASTM A508 steel tested at 175° F.

The finite element model simulates a fracture test at 175° F. for the material. FIGS. 14 through 16 demonstrate the success of the stress field modification in achieving nearly plane strain conditions. A two dimensional plane strain finite element model was run to obtain the solution for an infinitely thick plate. The three dimensional side pull solution closely approximates the two dimensional plane strain results.

Figure 17:
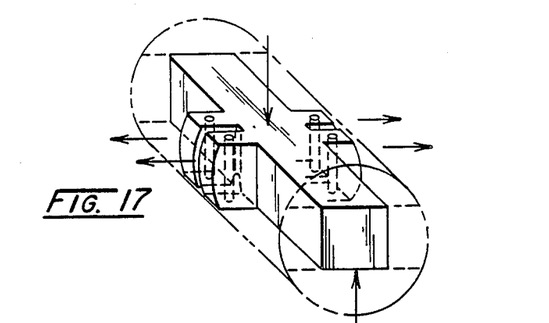
FIG. 17 shows a perspective view of a miniature dynamic plane-strain crack initiation and arrest specimen prepared from rod product form.

Using the stress field modified approach, dynamic plane-strain crack-initiation ($K_{Id}$) and crack-arrest ($K_{Ia}$) fracture toughness can be determined. The side-load configuration shown in FIGS. 3, 5, 6, 7, 8, 9, 10, and 11 as well as other configurations can be used to test miniature crack initiation and arrest specimens. Modification to the specimen design for testing rods is shown in FIG. 17. The specimen can be cut directly from the rods, and there is no need for welding side-pull tabs or crack starter material.

The specimens are pre-fatigued so that $K_{Id}$, as well as $K_{Ia}$, can be determined. The pre-fatigued crack is long enough to ensure that the influence of the stress field associated with the notch is negligible. A blunt notch is not required, as is used with duplex specimens, since there is no need to propagate the crack past the weld line. A short crack-run and -arrest length can minimize dynamic effects. In ferritic steels, crack speeds on the order of 20,000 in./sec are typically observed with longitudinal wave speeds about a factor of 10 higher. Therefore, the reflected stress wave effect for a crack extension-arrest length of 0.1 in., or less, would be expected to be minimal. In very small specimens, dynamic effects must be accounted for using the finite element method. A three dimensional dynamic finite element analysis is performed to account for the effects of the reflected stress waves.

Servo-hydraulic test equipment can achieve ram velocities up to 20 in./sec, and ram velocities up to about 200 in./sec can be achieved with equipment modification. At speeds higher than about 5 in./sec, load transducer output oscillations can occur which require load frame resonant frequency corrections to the data. While these corrections can be made, it is best to avoid such difficulties when possible.

Figure 18:
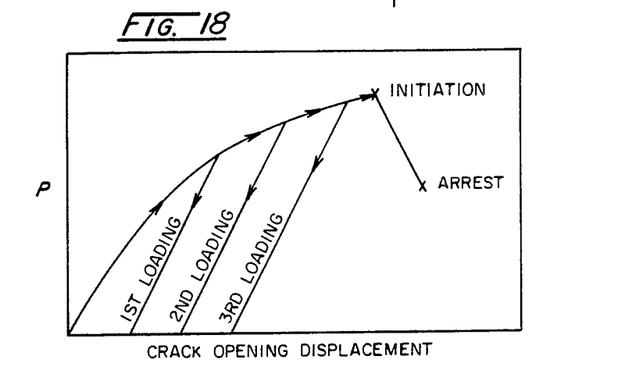
FIG. 18 is a graph showing a three point bend progress loading and unloading strategy to measure dynamic plane strain crack initiation and arrest fracture toughness.
Figures 19, 20:
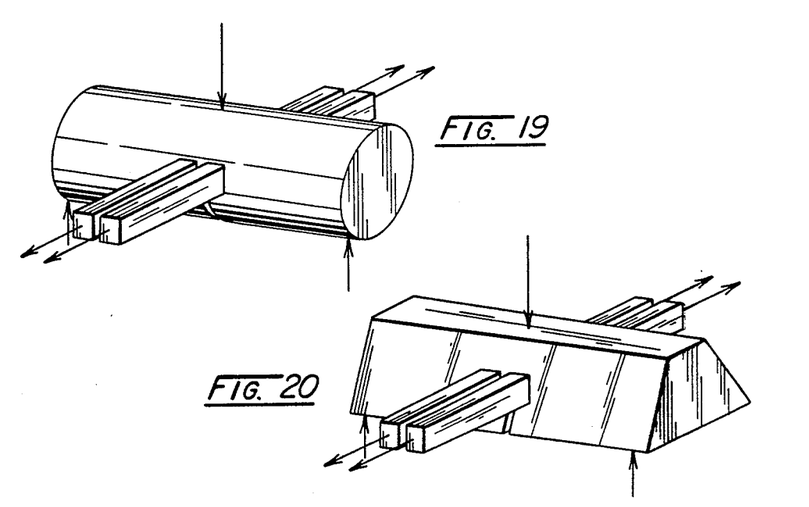
FIG. 19 is a perspective view of another embodiment of a specimen used in the method of this invention.
FIG. 20 is a perspective view of still another embodiment of a specimen used in the method of this invention.

There many ways to load the specimen and two useful methods are described. In the first, adjustable stop blocks are used to limit the amount of energy deposited in the specimen. The goal here is to minimize interaction with the servo-system. It is desirable to allow the elastic stored energy to drive the crack and minimize the energy contribution to crack extension from the servo-system. This can be accomplished through progressively higher load applications until initiation occurs, as shown in FIG. 18. Using this loading scenario it is possible to make a direct measurement of the initiation and arrest load. As a cross check, it is useful to measure the specimen compliance and use the final crack-opening-displacement (COD) and crack length to check the direct load measurements.

The specimen compliance measurements are made with the side-load applied for several crack lengths. The crack lengths can be cut using fine-continuous wire EDM.

The second loading approach is to use a computer-controlled servo-system to stop the ram while in contact with the specimen and reverse its direction. Computer controlled software can be used to perform this type of loading history. The method of progressive loading is also used. From the ram trip point to zero velocity, there is, a short period of deceleration. If initiation occurs just prior to, or shortly after the trip point is encountered, the ram would be in contact with the specimen and provide data for determination of the arrest load.

The COD can be measured using an eddy current transducer (ECT). A small tab is attached to the specimen near the notch. An optical extensometer can be used to calibrate the ECT at room temperature. It is preferable to use the optical extensometer to make the displacement measurements during testing below room temperature, however, difficulties can be encountered at temperatures below about 0° F. due to frost becoming dislodged on impact. During calibration, the accuracy of the eCT is checked when rotation of the tab occurs in addition to displacement. If necessary, a data correction can be applied to account for rotation.

As described earlier, a finite element analysis is performed to determine the amount of side-load needed to ensure that plane-strain conditions are achieved in the vicinity of the crack tip.

It is also possible to use the method of this invention to determine the fracture mode transition behavior (FMTB) of solid materials. The ASTM standard for determining FMTB is ASTM E23. In the prior art, it is not generally required that plane-strain conditions prevail for FMTB testing. The method of this invention can be used to induce a stress field in a miniature specimen which results in a stress field similar to ASTM E23 specimens. The FMTB from the miniature specimens would closely approximate that of the conventional specimens.

It is herein understood that although the present invention has been specifically disclosed with the preferred embodiments and examples, modifications and variations of the concepts herein disclosed may be resorted to by those skilled in the art. Such modifications and variations are considered to be within the scope of the invention and the appended claims.

The following references are incorporated herein:

(1) "Plane-Strain Fracture Toughness of Metallic Materials", ASTM E399-83, Volume 3.01, Metals—Mechanical Testing', Elevated and Low-Temperature Tests, American Society for Testing Materials (2) "Standard Test Method for $J_{IC}$, A Measure of Fracture Toughness", ASTM E813-81, Volume 3.01, Metals—'Mechanical Testing'; Elevated and Low-Temperature Tests, American Society for Testing and Materials (3) R. W. Hertzger, "Information and Fracture Mechanics of Engineering Materials", Second Edition, John Wilz and Sons, 1983.

(4) "Statistical Analysis of Cleavage-Fracture Data", Manahan et al.—Paper presented Int. Conf. and Exhibit- Salt Lake City, Dec. 2-6, 1985

(5) "Pressure Vessel Fracture Studies Pertaining to the PWR Thermal-Shock Issue Experiements" TSE-5, TSE-5A, and TSE-6, R. D. Cheverton, et al, WU-REG/CR-4249, ORNL-616

I claim:

1. A process of determining mechanical behavior of solid material, comprising:
   (a) providing a specimen of the material having a volume and smallest dimension sufficient to establish continuum behavior in all directions, and with a volume not more than $10^7$ times said sufficient volume;
   (b) modifying the stress field of the specimen by applying a first load to the specimen so as to induce and/or modify the existing stress field in the specimen and obtain a selected stress state;
   (c) deforming the specimen by applying a second load on the specimen in a direction different than the orientation of the first load of (b) above;
   (d) measuring at least one key variable in step c; and
   (e) determining the behavior of the material from the measurements taken according to the principles of the finite element method and/or the principles of linear or nonlinear material mechanics or both.

2. A process according to claim 1 wherein step (b) includes applying the stress field modifying first load by means of a tensile force at positions juxtaposed to the crack plane.

3. A process according to claim 2 wherein the specimen is solid and of three dimensional rectangular shape, having three pairs of parallel sides, and the first load is applied on two opposite sides and the second load is applied to two other sides.

4. A specimen according to claim 2 wherein the side member means protrude laterally from the elongate sides of the specimen at the position of the attachment of the load means so that a tensile force can be applied to opposite sides of the specimen simultaneously.

5. A process according to claim 1 wherein step (b) includes applying the stress field modifying first load by means of a moment at positions juxtaposed to the crack plane.

6. A process according to claim 1 wherein step (b) includes applying the stress field modifying first load by means of a magnetic field induced to positions juxtaposed to the crack plane.

7. A process of determining fracture behavior of solid material, comprising:
   (a) providing a specimen of the material having a volume and smallest dimension sufficient to establish continuum behavior in all directions, and with a volume not more than $10^7$ times said sufficient volume, notching and/or precracking the specimen;
   (b) modifying the stress field of the specimen by applying a first load to the specimen so as to induce and/or modify the existing stress field and to result in a selected stress state, the magnitude of the induced stress being defined by analyses according to the principle of the finite element method and/or the principles of linear or nonlinear material mechanics or both,
   (c) applying a second load to the specimen in a direction different than the orientation of the first load of (b), the magnitude of the applied load being independent and the load of (c) depending on the load,
   (d) measuring $K_{IC}$, the plane strain fracture toughness, and/or $K_{Id}$, plane strain dynamic crack initiation fracture toughness, and/or $K_{Ia}$, plane strain dynamic crack arrest fracture toughness, and/or the J-Integral and/or fracture mode transition behavior, by increasing the loads (b) and (c) applied to the specimen until a crack propagates across a plane of the specimen,
   (e) determining the fracture behavior of the material from the measurements taken according to the principles of the finite element method and/or the principles of linear or nonlinear material mechanics or both.

8. A process according to claim 7 wherein $K_{Ia}$ and $K_{Id}$ are determined by using adjustable stop blocks to limit the amount of energy deposited in the specimen, and progressively higher loads are applied until crack initiation occurs.

9. A process according to claim 7 wherein $K_{Ia}$ and $K_{Id}$ are determined using a computer controlled servo system to stop the ram while in contact with the specimen and reverse its direction using progressively higher loads until crack initiation occurs.

10. In the process of determining the mechanical behavior of solid materials, comprising:
   a. providing a specimen of the material having at least a volume and smallest dimension sufficient to satisfy continuum behavior in all directions, and with the volume not More than $10^7$ times said sufficient volume;
   b. deforming the specimen by applying a first load on the specimen;
   c. measuring at least one key variable in step b, and
   d. determining the fracture behavior of the material from the measurements taken according to the principles of the finite element method, and/or linear or nonlinear material mechanics or both, and/or determining other mechanical behavior of the material from the measurements taken, according to the principles of the finite element method and/or linear or nonlinear material mechanics or both, an improvement comprising, during step b, modifying the stress field of the specimen by applying at least one second load to the specimen so as to induce and/or modify stress in the specimen.

11. A process according to claim 10 wherein the applied loads and/or the displacement and/or the crack opening, and/or the crack length, and/or the temperature of the specimen are measured as a function of time.

12. A specimen of solid material having a volume of smallest dimension sufficient to establish continuum behavior in all directions, and with a volume not more than $10^7$ times said sufficient volume; said specimen being constructed as a elongated beam like shape including three pairs of parallel sides; and having a notch intermediate to the ends and on one elongated side, with the notch protruding into each of the contiguous opposing elongated sides; and being further provided with at least one side member for the attachment of a load transmitting pre-stressing means to the specimen.

13. A process of determining fracture behavior of solid material, comprising:
   (a) providing a specimen of the material, and notching and/or precracking the specimen thereby providing for a generally planar crack across the specimen:
   (b) modifying the stress field of the specimen by applying a first load to the specimen so as to induce and/or modify the existing stress field and to result in a selected stress state, the magnitude of the induced stress being defined by analyses according to the principles of the finite element method and/or the principles of linear or nonlinear material mechanics or both;
   (c) applying at least one additional load to the specimen in a direction different than the orientation of the first load of (b), the magnitude of the applied first load being independent, and the magnitude of the additional load of (c) depending on the applied first load,
   (d) measuring $K_{IC}$, the plane strain fracture toughness, and/or $K_{Id}$, plane strain dynamic crack initiation fracture toughness, and/or $K_{Ia}$, plane strain dynamic crack arrest toughness, and/or the J-Integral and/or fracture mode transition behavior, by increasing the loads (b) and (c) applied to the specimen until a crack propagates across a plane of the specimen; and
   (e) determining the fracture behavior of the material from the measurements taken according to the principles of the finite element method and/or the principles of linear or nonlinear material mechanics or both.

14. A process according to claim 13 wherein step (b) includes applying the stress field modifying first load by means of a tensile force at positions juxtaposed to the crack induced and propagated in the plane of the notching and/or precracking to further generate the crack in said crack plane.

15. A process according to claim 14 wherein the specimen is solid and of three dimensional rectangular shape, having three pairs of parallel sides, and the first load is applied on two opposite sides and the second load is applied to two other sides.

16. A specimen according to claim 15 wherein the side member means protrude laterally from the elongate sides of the specimen at the position of the attachment of the load means so that a tensile force can be applied to opposite sides of the specimen simultaneously.

17. A process according to claim 13 wherein step (b) includes applying the stress field modifying first load by means of a moment at positions juxtaposed to the crack plane.

18. A process according to claim 13 wherein step (b) includes applying the stress field modifying first load by means of a magnetic field induced to positions juxtaposed to the crack plane.

19. A process according to claim 13 wherein $K_{Ia}$ and $K_{Id}$ are determined by using adjustable stop blocks to limit the amount of energy deposited in the specimen, and progressively higher loads are applied until crack initiation occurs.

20. A process according to claim 13 wherein $K_{Ia}$ and $K_{Id}$ are determined using a computer controlled servo system to stop the ram while in contact with the specimen and reverse its direction using progressively higher loads until crack initiation occurs.

21. In the process of determining the mechanical behavior of solid materials, comprising;
   (a) providing a specimen of the material;
   (b) deforming the specimen by applying a first load on the specimen;
   (c) measuring at least one key variable in step b; and
   (d) determining the fracture behavior of the material from measurements according to the principles of the finite element method and/or linear or nonlinear material mechanics or both, and/or determining other mechanical behavior of the material from the measurements taken, according to the principles of the finite element method and/or linear or nonlinear material mechanics or both,
   (e) an improvement comprising, during step b; modifying the stress field of the specimen by applying at least one second load to the specimen so as to induce or modify stress in the specimen.

22. A process according to claim 21 wherein the applied loads and/or the displacement and/or the crack opening, and/or the crack length, and/or the temperature of the specimen are measured as a function of time.

23. A specimen of solid material constructed as a elongated beam-like shape including three pairs of parallel sides; and having a notch intermediate to the ends and on one elongated side, with the notch protruding into each of the contiguous opposing elongated sides; and being further provided with at least one side member for the attachment of a load transmitting pre-stressing means to the specimen.

* * * * *